United States Patent
Kelman et al.

(10) Patent No.: US 8,751,198 B2
(45) Date of Patent: Jun. 10, 2014

(54) VARIABLE STIFFNESS STEM FOR PROSTHETIC IMPLANTS

(75) Inventors: David C. Kelman, Collierville, TN (US); Michael A. Croxton, The Woodlands, TX (US); Charles Wayne Allen, Southaven, MS (US); William L. Waltersdorff, Hernando, MS (US)

(73) Assignee: Smith & Nephew, Inc., Memphis, TN (US)

( * ) Notice: Subject to any disclaimer, the term of this patent is extended or adjusted under 35 U.S.C. 154(b) by 1266 days.

(21) Appl. No.: 12/442,326

(22) PCT Filed: Sep. 20, 2007

(86) PCT No.: PCT/US2007/079063
§ 371 (c)(1),
(2), (4) Date: Feb. 3, 2010

(87) PCT Pub. No.: WO2008/036831
PCT Pub. Date: Mar. 27, 2008

(65) Prior Publication Data
US 2010/0131245 A1 May 27, 2010

Related U.S. Application Data

(60) Provisional application No. 60/826,336, filed on Sep. 20, 2006.

(51) Int. Cl.
*G06F 17/50* (2006.01)
*G06F 7/60* (2006.01)

(52) U.S. Cl.
USPC .................................................. 703/1; 703/2

(58) Field of Classification Search
CPC ............ G06F 17/50; G06F 7/60; G06T 17/20
USPC ........................................................... 703/1, 2
See application file for complete search history.

(56) References Cited

U.S. PATENT DOCUMENTS

| 5,594,651 | A | * | 1/1997 | St. Ville | 700/98 |
| 6,093,209 | A | | 7/2000 | Sanders | |
| 7,203,628 | B1 | * | 4/2007 | St. Ville | 703/1 |
| 2006/0004465 | A1 | | 1/2006 | Bergin et al. | |

OTHER PUBLICATIONS

Engh and Bobyn, "The Influence of Stem Size and Extent of Porous Coating on Femoral Bone Resorption After Primary Cementless Hip Arthroplasty", Jun. 1, 1988, Clinical Orthopaedics and Related Research, No. 231, pp. 7-28.*

(Continued)

*Primary Examiner* — Mary C Jacob
*Assistant Examiner* — Juan Ochoa
(74) *Attorney, Agent, or Firm* — Krieg DeVault LLP

(57) ABSTRACT

A method for forming an implant for a bone including the steps of generating a first general shape for the implant having a length extending along a long axis of the bone, determining an area moment of inertia of a cross section of the implant, determining an area moment of inertia for a cross section of bone coplanar to the cross section of the implant, calculating a percent stress shielding from the area moments of inertia of the implant and the bone, comparing the calculated percent stress shielding to a preset threshold, and iteratively generating additional general shapes for the implant by locally adjusting the cross section of the implant until the calculated percent stress shielding meets the preset threshold.

27 Claims, 2 Drawing Sheets

(56) References Cited

OTHER PUBLICATIONS

Kuiper and Huiskes, The predictive value of stress shielding for quantification of adaptive bone resorption around hip replacements, 1997, Journal of Biomechanical Engineering, vol. 119, pp. 228-231.*

Gross and Abel, A Finite Element Analysis of Hollow Stemmed Hip Prostheses As a Means of Reducing Stress Shielding of the Femur, Aug. 2001, Journal of Biomechanics 34; pp. 995-1003.*

Ramos et al., A Preliminary Investigation on The Influence of Cross Section Geometry on Cemented Interface Stresses in Femoral Hip Replacements, Jun. 29 2003, Summer Bioengineering Conference, pp. 0727-0728.*

Huiskes et al., Adaptive Bone Remodeling and Biomechanical Design Considerations, Sep. 1989, Orthopedics, pp. 1255-1267.*

Makarand Joshi et al., Analysis of a Femoral Hip Prosthesis Designed to Reduce Stress Shielding, 2000, Journal of Biomechanics 33, pp. 1655-1662.*

Kidder et al., 3D Model Acquisition, Design, Planning and Manufacturing of Orthopaedic Devices: A Framework, Dec. 1996, SPIE vol. 2911, Advanced Sensor and Control-System Interface, pp. 9-22.*

Chang et al., Design and Analysis of Robust Total Joint Replacements: Finite Element Model Experiments with Environmental Variables, Jun. 2001, Journal of Biomechanical Engineering, vol. 123, pp. 239-246.*

International Search Report, PCT/US2007/079063, Jan. 7, 2008, 3 pages.

International Preliminary Report on Patentability, PCT/US2007/079063, Mar. 24, 2009, 6 pages.

Charles A. Engh et al., "The Influence of Stem Size and Extent of Porous Coating on Femoral Bone Resorption after Primary Cementless Hip Arthroplasty", Clinical Orthopaedics and Related Research, Jun. 1988, pp. 7-28, No. 231.

Matthew J. Silva et al., "Reduced Bone Stress as Predicted by Composite Beam Theory Correlates with Cortical Bone Loss following Cemented Total Hip Arthroplasty", Journal of Orthopaedic Research, 1999, pp. 525-531, vol. 17 No. 4, Copyright 1999 Orthopaedic Research Society.

* cited by examiner

VARIABLE STIFFNESS STEM FOR PROSTHETIC IMPLANTS

CROSS-REFERENCE TO RELATED APPLICATIONS

This application is a U.S. National Phase filing of International Application No. PCT/US2007/079063 which claims the benefit of U.S. Provisional Application No. 60/826,336, filed Sep. 20, 2006. The applications are herein incorporated by reference.

BACKGROUND OF THE INVENTION

1. Field of the Invention

This invention relates generally to prosthetic implants having stem portions and, more particularly, to prosthetic implants having stem portions subject to issues of stress shielding in implant.

2. Related Art

Total hip arthroplasty (THA) is an extremely successful surgical technique. With the improvements in varying technologies including cross-linked polyethylenes, metal-on-metal, and ceramic bearings appear to minimize long-term issues related to bone loss due to osteolysis. Now the attention is once again focused on bone maintenance particularly due to effects of the presence of an implant within the femur. A composite beam of the femur and implant is created during surgery. This composite beam results in the stresses being shared between the femur and the implant. The bone, then, is exposed to lower stress levels when the implant supports more of the load.

In 1892, Wolff postulated that the bony struts (Trabecular) of the proximal femur were aligned with the principal structure. Huskes in 1992, one hundred years later, has stated that flexible stems do reduce stress shielding in bone remodeling. Sychtez reported in 2001 that the axial stiffness of the femur accounts for approximately 46% of the variance of the loss of bone. This was the most significant factor influencing atrophy. Another major contributor to bone loss is the implant design itself. In addition to the femur and the implant, patient parameters such as physiological loading, activity levels, etc, may contribute to the remodeling of the femur.

There remains a need in the art for a method to establish design parameters for orthopaedic implants by adjusting local stiffness of implant, based upon combined stiffness of implant/bone composite to minimize stress shielding.

SUMMARY

It is in view of the above problems that the present invention was developed. A method for forming an implant for a bone may comprises the step of generating a first general shape for the implant having a length extending along a long axis of the bone. A step may determine an area moment of inertia of a cross section of the implant. The step may also determine an area moment of inertia for a cross section of bone coplanar to the cross section of the implant. A percent stress shielding may be calculated from the area moments of inertia of the implant and the bone. A step may compare the calculated percent stress shielding to a preset threshold. Iteratively, additional general shapes may be generated for the implant by locally adjusting the cross section of the implant until the calculated percent stress shielding meets the preset threshold.

An embodiment provides determining an area moment of inertia for a cross section of bone step is determined from radiographic information of the patient.

An embodiment further comprises the step of setting a modulus of elasticity of the implant and the bone.

Another embodiment provides the modulus of elasticity of the bone is calculated from the quality of the bone.

Yet another embodiment provides the quality of bone is calculated from radiographic information of the patient.

An embodiment further comprises the step of iteratively performing the determining steps, the calculating step, the comparing step and the iteratively generating additional general shapes step along the length of the implant.

Another embodiment provides the iteratively performing step is performed at positions equally spaced from one another.

Yet another embodiment provides the iteratively performing step is performed incrementally closer to adjacent cross sections when the cross section of the implant along the length of the implant changes.

Another embodiment provides the iteratively performing step is performed incrementally closer to adjacent cross sections when the cross section of the bone along the length of the implant changes.

Yet another embodiment provides the iteratively performing step is performed incrementally closer to adjacent cross sections when the quality of the bone along the length of the implant changes.

An embodiment provides the percentage stress shielding is calculated using the equation: Percentage Stress Shielding= $[1-\{1/(1+N(I_I/I_B))\}]*100$;

where N=ratio of modulus of elasticity= $E_{implant}/E_{bone}$;
$I_I$=area moment of inertia of implant, and
$I_B$=area moment of inertia of bone.

A system for creating an implant for implantation in a bone may comprise an initial representation of an implant member configured to extend along the length of the bone. The first member may have a cross section. The cross sections have an area moment of inertia. The system may further comprise bone information relating to the quality and dimensions of the bone. The bone information may provide an area moment of inertia for a cross section of bone coplanar to the cross section of the implant. A percent stress shielding from the area moments of inertia of the implant and the bone may be calculated and compared to a preset threshold. The system may further comprise an iterative representation of an implant member generated by locally adjusting the cross section of the implant until the calculated percent stress shielding meets the preset threshold such that the initial representation is changed to the iterative representation.

An embodiment provides the bone information is determined from radiographic information of the patient.

Another embodiment provides the initial representation further comprises the modulus of elasticity of the implant and the bone information comprises the modulus of elasticity of the bone.

Yet another embodiment provides the modulus of elasticity of the bone is calculated from the quality of the bone.

Another embodiment provides the quality of bone is calculated from radiographic information of the patient.

An embodiment further comprises additional cross sections of the implant along the length of the bone.

Another embodiment provides the additional cross sections are positioned equally spaced from one another.

Yet another embodiment provides the additional cross sections are positioned incrementally closer to adjacent cross sections when the cross section of the implant along the length of the implant changes.

Another embodiment provides the additional cross sections are positioned incrementally closer to adjacent cross sections when the cross section of the bone along the length of the implant changes.

Yet another embodiment provides the additional cross sections are positioned incrementally closer to adjacent cross sections when the quality of the bone along the length of the implant changes.

Another embodiment provides the percentage stress shielding is calculated using the equation:

Percentage Stress Shielding=$[1-\{1/(1+N(I_I/I_B))\}]$ *100;

where N=ratio of modulus of elasticity=$E_{implant}/E_{bone}$;
$I_I$=area moment of inertia of implant, and
$I_B$=area moment of inertia of bone.

Further features, aspects, and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate embodiments of the present invention and together with the description, serve to explain the principles of the invention. In the drawings.

DETAILED DESCRIPTION OF THE EMBODIMENTS

Figure 1:
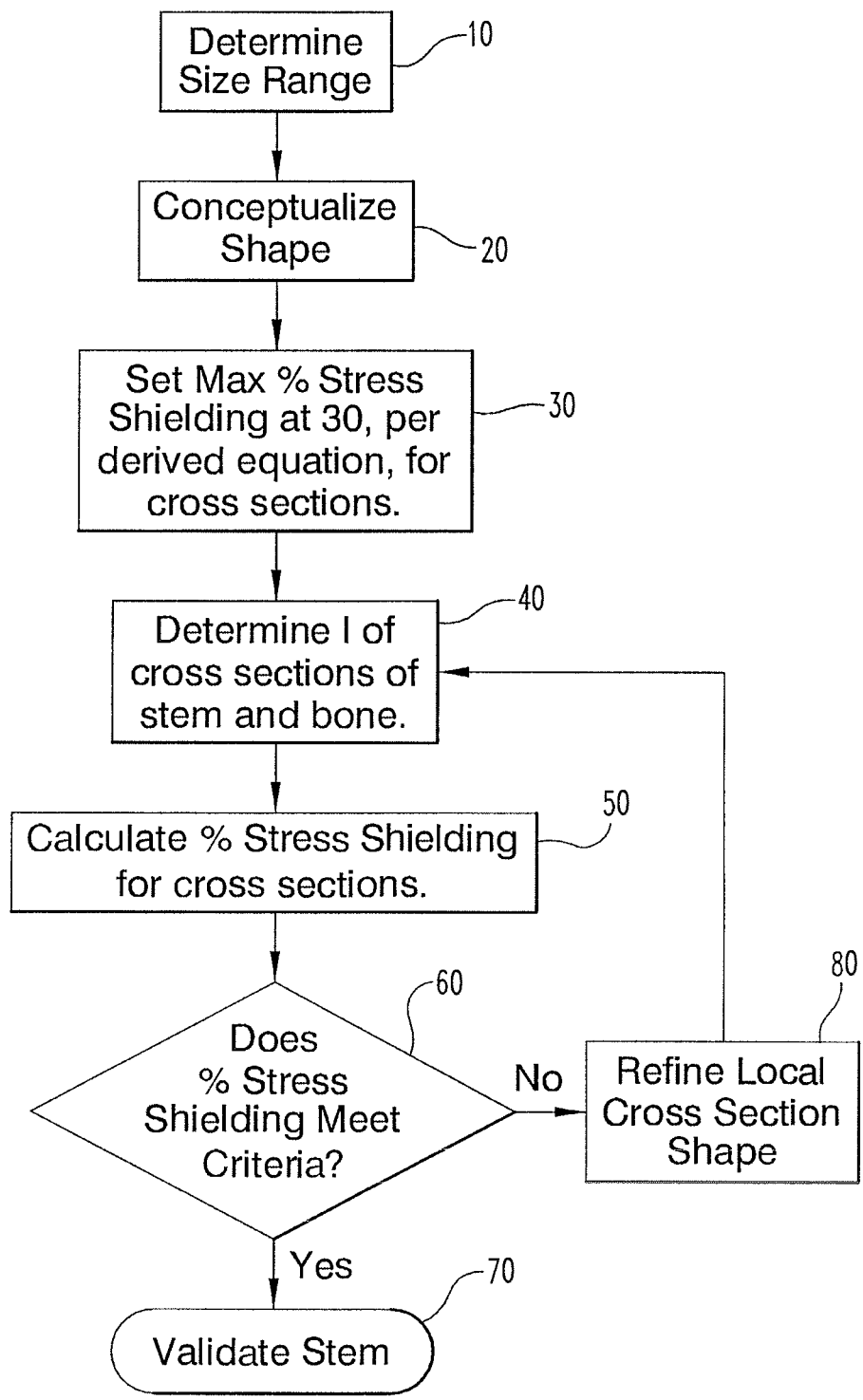
FIG. 1 is a flowchart illustrating method steps for setting the cross section of an orthopaedic implant for a specific stiffness relative to the stiffness of the bone.

Referring to the accompanying drawings in which like reference numbers indicate like elements, FIG. 1 is a flowchart illustrating method steps for setting the cross section of an orthopaedic implant for a specific stiffness relative to the stiffness of the bone. The flowchart specifically sets the stiffness of a hip stem, but other orthopaedic implants where stress shielding of bone under composite beam loading of the implant and the bone occur may similarly be designed according to the methods of FIG. 1. In step 10, a size range is determined for the orthopaedic implant. Step 20 conceptualizes a shape for the implant. A target percentage stress shielding is set in step 30. In step 40, the moment of inertia is calculated for both the bone and the implant. Step 50 calculates the stress shielding percentage of the implant. In step 60, there is a decision inquiring whether the percentage stress shielding meets the criteria for the local (i.e., individual) cross sections. If so, then the analysis is complete and the designer moves on to step 70 of design validation. If not, then the designer goes to step 80 to refine the local cross section shape and returns to step 40.

Step 10 includes determining a size range for the implant. This may include identifying a particular population to receive the orthopaedic implant, retrieving published data on the identified population, and selecting implant sizes that correlate with the published data. For example, the designer may select a certain segment of the Japanese female population, identify femur sizes from available public data, and select hip stem implant sizes that correlate with the identified femur sizes.

The initial goal of any cementless THA procedure is to gain stability of the implant. Regardless of the philosophy being utilized, for example distal fixation or proximally loaded implant, the implant is selected by the largest possible implant permitted by the internal dimensions of the femur. Thus, generally, size is maximized for stability based upon the bone in which the implant will be implanted. Surgeon specification and comfort may also limit the implant size.

Further size ranges may be based on business decisions, such as manufacturing costs, marketing data, or other factors that generally relate to the decision of whether or not it is cost effective to provide a product. A size range may be selected upon on the any number of economic factors. Further, a size range may be selected based upon material properties of the material selected for the implant.

Next in step 20, the designer conceptualizes a shape for the orthopaedic implant. The design concept may be based upon desired characteristics of the implant, such as implant general shape, whether or not it should be anatomically matching, or whether the implant should contact certain regions of bone. The conceptualized design provides the baseline cross section or sections for analysis.

Next in step 30, a target percentage stress shielding is selected. Referring back to the work of Dr. Charles Engh, Engh's work provides analysis for percentage stress shielding. The work suggests stress shielding above 45 percent results in significant bone loss, about 30 to about 45 percent may result in some bone loss, and less than 30 percent provided a tolerable amount of bone loss. Therefore, identifying implants that provide less than 30 percent stress shielding is highly desirable. Thus, as an example only, the target percentage stress shielding may be set to 30 in step 30.

In step 40, the area moment of inertia (or alternatively called the second moment of area or second moment of inertia) is calculated for each cross section of the implant and the corresponding cross section of bone, that is the bone portion coplanar with the cross section of the implant when the implant is positioned within the bone. The moment of inertia may be calculated by hand or through the use of a computer-aided design module. The area of cross section of bone may be approximated using publicly available data. Alternatively, for a custom hip implant, a CAT scan may be used to measure bone data, and then utilizing the collected CAT scan data, calculate moments of inertia corresponding to the cross sections of the bone.

The area moment of inertia for the implant, given a circular cross section of the implant, is proportional to the diameter to the $4^{th}$ power. The bone corresponding to the same point along the longitudinal axis of the leg has an area moment of inertia calculated according to the difference between the diameter to the $4^{th}$ power of the outside diameter of the femur and the diameter to the $4^{th}$ power of the outside diameter of the implant (because the interface between bone and implant occurs at the outside diameter of the implant).

While this example has been limited to circular cross sections in an x-y plane, other cross sections that are not circular (or approximately circular) may be used. The mathematics may become more involved as circular cross sections have specific properties such that the area moment of inertia is the same in the x and y directions, while other cross sections would require calculations of the moments of inertia in each the x and y direction. By examining the moments of inertia of the cross sections, the analysis examines the bending stresses in multiple planes instead of a single plane.

In step 50, the percentage stress shielding is calculated using the moments of inertia from step 40. The improved equation is as follows:

$$\text{Percentage Stress Shielding} = [1 - \{1/(1+N(I_I/I_B))\}] * 100;$$

where N=ratio of modulus of elasticity=$E_{implant}/E_{bone}$;
$I_I$=area moment of inertia of implant, and
$I_B$=area moment of inertia of bone.

In step 50, the designer plugs in the moment of inertia for the implant cross section and the bone cross section from step 40 into the above formula and calculates the percentage stress shielding. The elastic modulus for the implant, would be known based upon the material. The elastic modulus of the bone may be a function of patient specific data, or may be gathered from population data. For a patient specific implant, the elastic modulus of the bone would be based upon radiographic data, and may be affected by patient specific attributes such as bone density, gender, disease state, etc. Thus, as these factors vary along the length of the femur, the elastic modulus of the bone may vary along the length of the femur. The modulus of the implant may also vary, for example, in a composite implant where multiple materials of differing moduli are used, differences may occur if the relative amounts of the two different materials used in the composite implant are varied along the length of the implant. Because the modulus of elasticity of either the bone or the implant may vary, the ratio of the moduli of the implant to the bone may also vary along the length of the femur.

There exists approximately a 50% reduction in the modulus of elasticity by changing materials from CoCr to TI6-4. Comparing the stiffness of 12 mm CoCr cylindrical stem to that of a 14 mm TI 6-4 stem, results in similar stiffness implants. The reason for the limited benefit of material change to the stiffness of the implant is the fact that implant stiffness basically increases to the fourth order of the diameter while the modulus is a single order variable.

The process repeats until all of the local cross sections pass the decision step provided in step 60. The number of local cross sections taken may be chosen as close as necessary to be confident that the stress shielding is well calculated along the length. For rapidly changing cross sections of femur and/or implant, more cross sections closer together may be desirable, while for relatively constant areas of femur and implant, fewer local cross sections may be taken. Additionally, if the area moment of inertia and the moduli of elasticity of the bone and implant can be described as a function of the longitudinal axis of the femur, then the function can be integrated and calculated using integral calculus.

The validation step 70 may include any number of standard methods for validating initial designs. This may include evaluating yield strength, hardness, fatigue strength or other mechanical properties. Further, validation may include other tests for surface texture, porous coatings, or other surface enhancements.

Although the method has been described in conjunction with a hip stem example, those of ordinary skill in the art would understand that the invention could be applied to any orthopaedic implant including, but not limited to, shoulder implants and knee implants.

By applying composite beam theory to the bone/implant composite, the present invention is not limited by the design constraint of typical implant which attempt to match the stiffness of bone and implant. The geometry of an implant may be altered to a certain stiffness that does not ignore the added stiffness of the surrounding bone in an attempt to reduce the load transferring between bone and implant.

Figure 2:
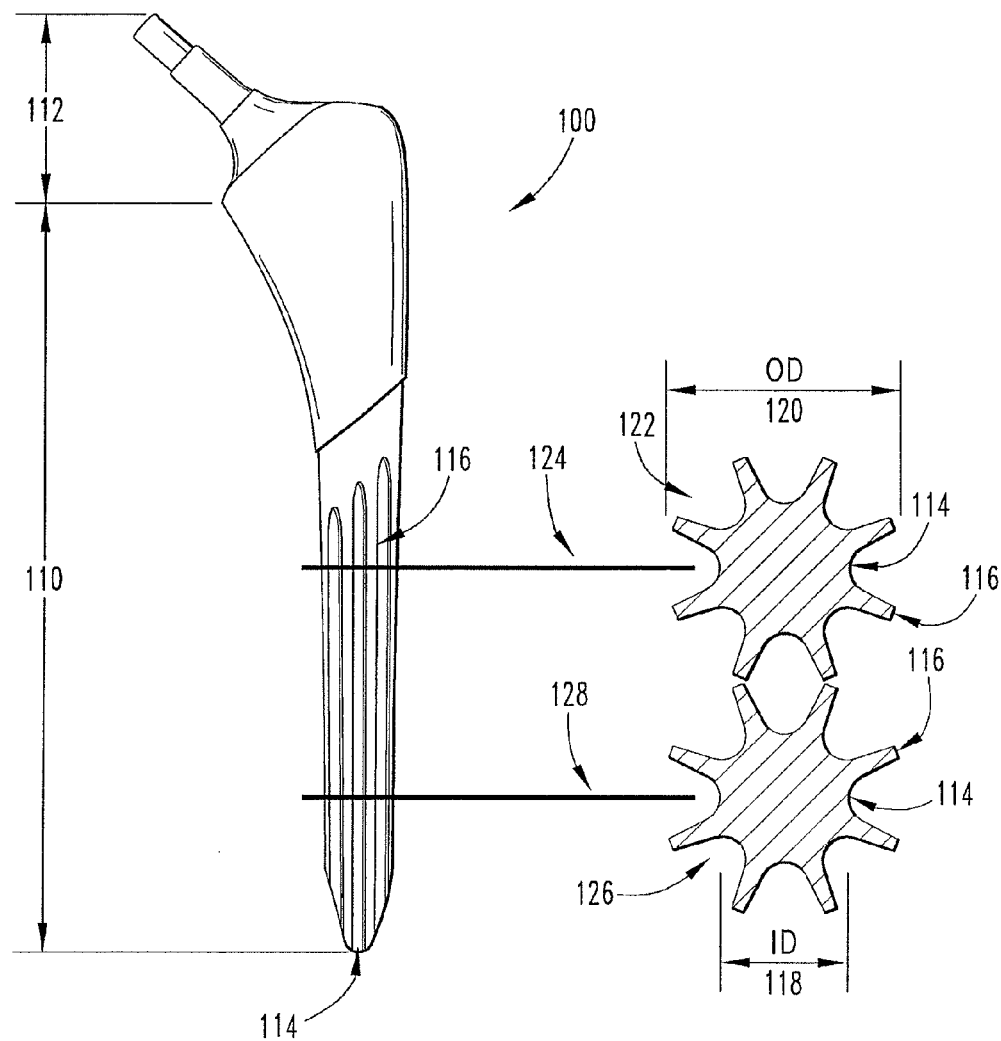
FIG. 2 is an example of an implant.

FIG. 2 is an example of an implant 100. The implant 100 includes a stem portion 110 extending from a neck portion 112. A core portion 114 and flutes 116 on the stem portion 110 define an inner diameter ID 118 and an outer diameter OD 120, respectively. A proximal cross section 122 taken at a proximal portion 124 and a distal cross section 126 taken at a distal portion 128 of the stem 110 show differences as a function of the length along the stem 110.

The implant 100 may have a continuously changing cross section for the inner diameter 118 along the length of the stem portion 110 while maintaining a constant outside diameter 120 along the stem portion 110. This may be accomplished by feathering the flutes 116 such that the flutes 116 are radially small proximally along the stem portion 110 and radially larger distally along the stem portion 110. The flutes 116 provide minimal stiffness. When calculating the moment of inertia of the stem portion, most of the value of the moment of inertia is in the core portion 114 and not in the flutes 116. Thus, the percentage stress shielding may be kept relatively small by tapering the inner portion and reducing the moment of inertia of the implant 100. Additionally, the size of the implant may still be as large as possible because the flutes 116 may provide the additional outside diameter 120. By manipulating the cross section, which roughly varies with the $4^{th}$ power of the inner diameter 118 as previously discussed, the stiffness and thus the percentage stress shielding of the implant/bone may be minimized such that bone loss from the stress shielding may be lessened. While this implant 100 has adjusted the core diameter of the implant, other configurations such as changing a core material relative to an outer implant material and additionally changing the relative amounts of the core material to the outer material. Moreover, while this example has used a circular cross section, other cross sections which may vary the moments of inertia in the x-y plane of the cross section may allow for additional multi-plane variations of stiffness.

The shape of the cross section of the implant may be varied continuously, or may be varied sectionally. Similar to the process of calculating moments of inertia, the need to change the implant may be based upon the changes of the bone. For example, where along the femur the quality and width of the bone is rapidly changing, the implant may require more adjustment of the implant cross section. Thus, local bone stiffnesses may result in local changes to cross section without affecting other portions of the implant.

In view of the foregoing, it will be seen that the several advantages of the invention are achieved and attained.

The embodiments were chosen and described in order to best explain the principles of the invention and its practical application to thereby enable others skilled in the art, to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A method for forming an implant for a bone, comprising the steps of:

generating a first general shape for the implant having a length extending along a long axis of the bone;

determining an area moment of inertia of a cross section of the implant, wherein the area moment of inertia of the cross section of the implant is calculated using a computer-aided design module;

determining an area moment of inertia of a cross section of bone coplanar to the cross section of the implant, wherein the area moment of inertia of the cross section of bone coplanar to the cross section of the implant is calculated using the computer-aided design module;

calculating a percent stress shielding from the area moments of inertia of the implant and the bone;

comparing the calculated percent stress shielding to a preset threshold; and iteratively generating additional general shapes for the implant by locally adjusting the cross section of the implant until the calculated percent stress shielding meets the preset threshold, wherein the locally adjusting of the cross section of the implant comprises adjusting local stiffness of the implant based on combined stiffness of an implant and bone composite at the cross section of the implant to minimize stress shielding of the bone such that bone loss from the stress shielding may be lessened.

2. The method of claim 1, wherein the determining an area moment of inertia for a cross section of bone is determined from radiographic information of the bone.

3. The method of claim 1, further comprising the step of setting a modulus of elasticity of the implant and a modulus of elasticity of the bone.

4. The method of claim 3, wherein the modulus of elasticity of the bone is calculated from the quality of the bone.

5. The method of claim 4, wherein the quality of bone is calculated from radiographic information.

6. The method of claim 1, further comprising the step of iteratively performing the determining steps, the calculating step, the comparing step and the iteratively generating additional general shapes step along the length of the implant.

7. The method of claim 6, wherein the iteratively performing step is performed at positions equally spaced from one another.

8. The method of claim 6, wherein the iteratively performing step is performed incrementally closer to adjacent cross sections when the cross section of the implant along the length of the implant changes.

9. The method of claim 6, wherein the iteratively performing step is performed incrementally closer to adjacent cross sections when the cross section of the bone along the length of the implant changes.

10. The method of claim 6, wherein the iteratively performing step is performed incrementally closer to adjacent cross sections when the quality of the bone along the length of the implant changes.

11. The method of claim 1, further comprising the step of forming a prosthetic implant having a locally adjusted cross section wherein the calculated percent stress shielding meets the preset threshold; and implanting the prosthetic implant in the bone.

12. The method of claim 1, wherein the locally adjusting of the cross section of the implant results in minimizing stress shielding of the bone surrounding the implant when the implant is implanted in the bone.

13. The method of claim 1, wherein the locally adjusting of the cross section of the implant comprises altering geometry of the implant to reduce load transferring between the bone and the implant.

14. The method of claim 1, wherein the locally adjusting of the cross section of the implant comprises altering geometry of the implant to a stiffness that does not ignore added stiffness of the bone surrounding the implant to reduce load transferring between the bone and the implant.

15. The method of claim 1, wherein the percentage stress shielding is calculated using the equation:

$$\text{Percentage Stress Shielding} = [1-(1/(1+N(I_I/I_B)))]*100;$$

where N=ratio of modulus of elasticity=$E_{implant}/E_{bone}$, $I_I$=area moment of inertia of implant, and $I_B$=area moment of inertia of bone.

16. A method for forming an implant for a bone, comprising the steps of:

generating a first general shape for the implant having a length extending along a long axis of the bone;

determining an area moment of inertia of a cross section of the implant, wherein the area moment of inertia of the cross section of the implant is calculated using a computer-aided design module;

determining an area moment of inertia of a cross section of bone coplanar to the cross section of the implant, wherein the area moment of inertia of the cross section of bone coplanar to the cross section of the implant is calculated using the computer-aided design module;

calculating a percent stress shielding from the area moments of inertia of the implant and the bone;

comparing the calculated percent stress shielding to a preset threshold; and iteratively generating additional general shapes for the implant by locally adjusting the cross section of the implant until the calculated percent stress shielding meets the preset threshold; and wherein the percentage stress shielding is calculated using the equation:

$$\text{Percentage Stress Shielding} = [1-(1/(1+N(I_I/I_B)))]*100;$$

where N=ratio of modulus of elasticity=$E_{implant}/E_{bone}$, $I_I$=area moment of inertia of implant, and $I_B$=area moment of inertia of bone.

17. A system for creating an implant for implantation in a bone, comprising:

a computer-aided design module;

an initial representation of an implant member having an implant length configured to extend along the length of the bone, the implant member having cross sections along the implant length, the cross sections each having an area moment of inertia, wherein the area moment of inertia of the cross sections of the implant member are calculated by the computer-aided design module;

bone information relating to the quality and dimensions of the bone, the bone information providing an area moment of inertia for a cross section of bone coplanar to a corresponding one of the cross sections of the implant member, wherein the area moment of inertia of the cross section of bone coplanar to the corresponding one of the cross sections of the implant member is calculated by the computer-aided design module, wherein a percent stress shielding using the area moment of inertia of the cross sections of the implant member and the area moment of inertia of the cross section of the bone coplanar to the corresponding one of the cross sections of the implant member is calculated and compared to a preset threshold, wherein the percentage stress shielding is calculated using the equation:

$$\text{Percentage Stress Shielding} = [1-(1/(1+N(I_I/I_B)))]*100;$$

where N=ratio of modulus of elasticity=$E_{implant}/E_{bone}$,
$I_I$=area moment of inertia of implant, and
$I_B$=area moment of inertia of bone; and an iterative representation of an implant member generated by locally adjusting the corresponding one of the cross sections of the implant member until the calculated percent stress shielding meets the preset threshold whereby the initial representation is changed to the iterative representation.

18. The system of claim 17, wherein the bone information is determined from radiographic information of the bone.

19. The system of claim 17, wherein the initial representation further comprises the modulus of elasticity of the implant member and the bone information comprises the modulus of elasticity of the bone.

20. The system of claim 19, wherein the modulus of elasticity of the bone is calculated from the quality of the bone.

21. The system of claim 20, wherein the quality of bone is calculated from radiographic information.

22. The system of claim 17, further comprising additional cross sections of the implant member along the length of the bone.

23. The system of claim 17, wherein the additional cross sections are positioned equally spaced from one another.

24. The system of claim 22, wherein the additional cross sections are positioned incrementally closer to adjacent cross sections when the cross section of the implant member along the length of the implant member changes.

25. The system of claim 22, wherein the additional cross sections are positioned incrementally closer to adjacent cross sections when the cross section of the bone along the length of the implant member changes.

26. The system of claim 22, wherein the additional cross sections are positioned incrementally closer to adjacent cross sections when the quality of the bone along the length of the implant member changes.

27. The system of claim 17, further comprising a prosthetic implant having a locally adjusted cross section wherein the calculated percent stress shielding meets the preset threshold, the prosthetic implant sized and shaped for implantation in the bone.

* * * * *